(12) United States Patent
Shtyrlin et al.

(10) Patent No.: US 11,014,934 B2
(45) Date of Patent: May 25, 2021

(54) ANTISEPTIC DRUG

(71) Applicants: AO "TATKHIMFARMPREPARATY", Kazan (RU); Kazan Federal University, Kazan (RU)

(72) Inventors: Yurij G. Shtyrlin, Kazan (RU); Nikita V. Shtyrlin, Kazan (RU); Aleksej D. Strel'nik, Kazan (RU); Sergej V. Sapozhnikov, Kazan (RU); Al'fiya G. Iksanova, Kazan (RU); Renata R. Kazakova, Kazan (RU); Mariya N. Agafonova, Kazan (RU)

(73) Assignees: AO "Tatkhimfarpreparaty", Kazan (RU); Kazan Federal University, Kazan (RU)

( * ) Notice: Subject to any disclaimer, the term of this patent is extended or adjusted under 35 U.S.C. 154(b) by 9 days.

(21) Appl. No.: 16/751,861

(22) Filed: Jan. 24, 2020

(65) Prior Publication Data
US 2020/0157115 A1    May 21, 2020

Related U.S. Application Data

(63) Continuation of application No. PCT/RU2018/000379, filed on Jun. 7, 2018.

(30) Foreign Application Priority Data

Jul. 24, 2017   (RU) .............. RU2017126302

(51) Int. Cl.
| | | |
|---|---|---|
| *C07D 491/056* | (2006.01) | |
| *A61P 31/22* | (2006.01) | |
| *A61P 31/04* | (2006.01) | |
| *A61P 31/02* | (2006.01) | |
| *A61P 31/10* | (2006.01) | |

(52) U.S. Cl.
CPC .......... *C07D 491/056* (2013.01); *A61P 31/02* (2018.01); *A61P 31/04* (2018.01); *A61P 31/10* (2018.01); *A61P 31/22* (2018.01)

(58) Field of Classification Search
CPC ...... C07D 491/056; A61P 31/22; A61P 31/04; A61P 31/02; A61P 31/10
See application file for complete search history.

(56) References Cited

FOREIGN PATENT DOCUMENTS

| | | |
|---|---|---|
| RU | 2161961 C1 | 1/2001 |
| RU | 2561281 C1 | 8/2015 |
| RU | 2607522 C1 | 1/2017 |

OTHER PUBLICATIONS

International Search Report from PCT/RU2018/000379 dated Jun. 7, 2018, dated Sep. 6, 2018.

McDonnell G., et al. Antiseptics and Disinfectants: Activity, Action, and Resistance, Clinical Microbiology Reviews, Jan. 1999, pp. 147-179, vol. 12, No. 1.
Federal Register, Thursday, Jun. 30, 2016, vol. 81, No. 126, Proposed Rules.
Rasmussen, C.A., et al., Benzalkonium Chloride and Glaucoma, Journal of Ocular Pharmacology and Therapeutics, 2014, pp. 163-169, vol. 30, No. 2 & 3.
Kayumov, A.R. et al., Inhibition of biofilm formation in Bacillus subtilis by new halogenated furanones, The Journal of Antibiotics, 2015, pp. 297-301, vol. 68.
Herigstad, B. et al., How to optimize the drop plate method for enumerating bacteria, Journal of Microbiological Methods, 2001, pp. 121-129, vol. 44.
Morozova, N. S, et al., Modern view on the role of antiseptics in prevention and treatment of purulent septic complications at patients of surgical profile, Ukrainian journal of extreme medicine, named after G.O. Mozhaeva, 2012, pp. 6-9, v. 13, No. 2.
Pharmacology: textbook, edited by R. N. Alyautdin, 4th Edition, GEOTAR Media, 2010, p. 682, Chapter 36.
Schandala, M.G., Perspectives and Problems of Contemporary Disinfectology, Dezinfektsionnoe Delo, 2002, pp. 19-25, No. 3.
Miramistin, Register of Medicines of Russia, RLS Encyclopedia of Medicines—20th Edtion, Ch. Ed. G. L. Vyshkovsky, 2011, pp. 599, 600, LIBROPHARM.
Blatun, L.A., Miramistin in the Comprehensive Program of the Fight against Hospital Infections in the Surgical Hospital, Miramistin. Proceedings 1 Ed. Yu. S. Krivoshein.M., Medical News Agency, 2004, pp. 27-33.
Makeeva, M., et al., Administration of Miramistine in Combination Therapy of Mouth Mucous Membranes Diseases, Farmteka, 2013, pp. 33-38.
Fluomisin, https://www.vidal.ru/drugs/fluomisin_22520.

(Continued)

*Primary Examiner* — Timothy R Rozof
(74) *Attorney, Agent, or Firm* — Patentbar International, P.C.

(57) ABSTRACT

The invention refers to the chemistry of organic heterocyclic compounds, namely the new quaternary ammonium salt containing a fragment of vitamin $B_6$ derivative of formula I, showing antibacterial, antimycotic, antiviral and antiprotozoic properties. Compound can be used in medicine and veterinary medicine.

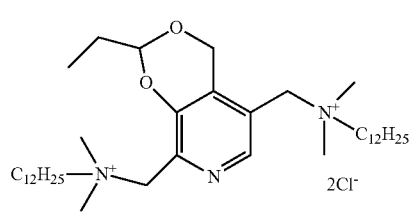

The invention can be used in medicine and veterinary medicine.

5 Claims, 2 Drawing Sheets

(56) References Cited

OTHER PUBLICATIONS

Benzalkonium Chloride, https://www.vidal.ru/drugs/dettol_benzalkonium_chloride_30527.

Guidelines MUK 4.2.1890-04, Definition of Microorganisms Sensitivity to Antibacterial Drugs, Control Methods. Biological and Microbiological Factors, 2004, Federal'nii tsentr gossanepidnadzora Minzdrava, Russia.

Methodological recommendations No. 2. Mycological examination of environmental objects and determination of antifungal activity of various substances, St. Petersburg Medical Academy of Postgraduate Education, 2008, pp. 14, 15, St. Petersburg.

GOST 32644-2014, Test Methods for Exposure to Chemicals on the Human Body, Moscow, 2015, Standartinform.

GOST 12.1.007-76, Occupational Safety Standards System Noxious Substances Classification and General Safety Requirements, Moscow, 2007, Standartinform.

Reinbaben, F., Antiviral Disinfection Basics, translation from German, Moscow, "Samarovon" LLC "Letniy sad" [Summer Garden] Publishing House, 2014, pp. 111-116.

Laboratory methods for the study and testing of medical prophylactic disinfectants to assess their effectiveness and safety: Guide-M. Federal Center for Hygiene and Epidemiology of Rospotrebnadzor, 2010, pp. 496-498.

Kuznetcov, D.P., et al., The Immunoenzymatic Diagnosticating of Infectious Rhinotracheitis in Cattle, Veterinary Medicine, 2002, v. 2, No. 5, pp. 17-18.

Shtyrlin, Yu. G. "Synthesis, structure and properties of heterocyclic compounds based on cis-2-butene-1,4-diol and pyridoxine" author's abstract of dissertation for the degree of Doctor of Chemical Sciences, Kazan 2016.

ANTISEPTIC DRUG

RELATED APPLICATIONS

This application is a Continuation application of International Application PCT/RU2018/000379, filed on Jun. 7, 2018, which in turn claims priority to Russian Patent Application RU2017126302, filed Jul. 24, 2017, both of which are incorporated herein by reference in their entirety.

FIELD OF THE INVENTION

The invention refers to the chemistry of organic heterocyclic compounds, namely the new quaternary ammonium salt containing a fragment of vitamin $B_6$ derivative of formula I, showing antibacterial, antifungal, antiviral and antiprotozoic properties. Compound can be used in medicine and veterinary medicine.

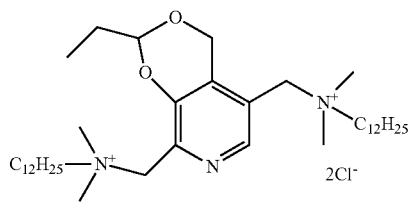

I

BACKGROUND OF THE INVENTION

The prevention and treatment of infectious diseases is currently one of the most important health challenges. Their effective therapy is possible only with the complex use of antibiotics and antiseptic drugs [Morozova N. S. *Modern view on the role of antiseptics in the prevention and treatment of purulent and septic complications in patients with surgical profile. The Ukrainian journal of extreme medicine named after G. O. Mozhaeva* [Morozova N. S. *Sovremennyy vzglyad na rol' antiseptikov v profilaktike i lechenii gnoyno-septicheskikh oslozhneniy u patsiyentov khirurgicheskogo profilya. Ukrainskiy journal ekstremalnoï medicini imeni G. O. Mozhaeva*, 2012—Vol. 13, No 2.—P.6-9].

A necessary requirement for antiseptics is the breadth of their spectrum of action: they must have antibacterial, antifungal, antiviral and antiparasitic activity [*Farmakologiya: uchebnik/Pod red. prof R. N. Alyautdina.*—4-*ye izd., pererab. i dop.*—*M: GEOTAR-Media,* 2010.—832 *s.*] *Pharmacology: textbook/Ed. prof RN. Alyautdina.*—4th ed., revised and updated—M.::GEOTAR-Media, 2010.—p. 832]. Due to their wide range of action antiseptics are used for many medical indications.

Quaternary ammonium compounds (QAC) are one of the most important classes of antiseptics and have a wide range of applications, particularly in the treatment of local purulent inflammatory processes, treatment of intact skin prior to surgery, preservation of eye drops, injection solutions, toothpastes, cosmetics, disinfection and surface cleaning. Modern QAC are characterized by a wide range of antimicrobial activity in relation to gram-positive and gram-negative microorganisms, fungi, viruses and protozoa. The mechanism of antibacterial action of QAC consists in their adsorption and penetration through the cell wall of bacteria with subsequent interaction with phospholipids of the cytoplasmic membrane, which leads to complete structural disruption and subsequent death of a bacterial cell [McDonnell G, Russell A D. *Antiseptics and Disinfectants: Activity, Action, and Resistance. Clinical Microbiology Reviews.*—1999—V. 12(1).—P. 147-179].

The disadvantages of the used QAC are inefficiency in relation to spores [Shandala M. G. *Perspektivy i problemy sovremennoy dezinfektologii. Zhurn. Dezinfektsionnoye delo.*—2002, No 4.—S 13-19. [Shandala M. G. *Prospects and problems of modern disinfectology. Journal Disinfection case.*—2002, No 4.—P 13-19] and simple viruses [Reinbaben, Friedrich von. *Osnovy protivovirusnoy dezinfektsii: perevod s nemetskogo yazyka—Moskva: Samarovo: Letniy sad.*—2014.—.S. 525]. Reinbaben, Friedrich von. *Fundamentals of antiviral disinfection: translation from German—Moscow: Samarovo: Summer garden.*—2014.—P. 525], as well as insufficient activity in relation to gram-negative bacteria, mycobacteria and fungi. There is also a lack of knowledge of the antiseptics used [*Federal Register*/ Vol. 81, No. 126/Thursday, Jun. 30, 2016/Proposed Rules] and their high toxicity [Rasmussen, C. A., Kaufman P. L., Kiland J. A. *Benzalkonium Chloride and Glaucoma. Journal of Ocular Pharmacology and Therapeutics.*—2014—V. 30.—P. 163-169.].

Among the drugs containing fragments of quaternary ammonium salts, it should be noted:

Miramistin ((benzyldimethyl [3-(myristoylamino) propyl]-ammonium chloride monohydrate) is an antiseptic developed in the USSR that has a wide spectrum of bactericidal action against gram-positive (*Staphylococcus* spp., *Streptococcus* spp., *Streptococcus pneumoniae*, etc.), gram-negative (*Pseudomonas aeruginosa, Escherichia coli, Klebsiella* spp. etc.), aerobic and anaerobic bacteria, pathogenic fungi and viruses, including clinical strains with polyresistance to antibiotics [*Registr lekarstvennyh sredstv Rossii RLS Entsiklopedia lekarstv* 20-*y yyp.Gl.red. G. L. Vyshkovskiy.*—*M.:LIBROFARM,* 2011.—S. 1368 [*The Register of Medicines of Russia RMR Encyclopedia of Drugs.*—20th issue chief. ed. D. L. Vyshkovskiy.—M.:LIBROPHARM, 2011. P. 1368]. It is used in prevention of suppurations and treatment of purulent wounds, treatment and prevention of candidiasis of the skin and mucous membranes, complex treatment of acute and chronic otitis, treatment and prevention of infectious and inflammatory diseases of the oral cavity (stomatitis, gingivitis, periodontitis, parodontitis), individual prevention of sexually transmitted diseases (syphilis, gonorrhea, chlamydiosis, genital herpes, etc.) [Blatun L. A. *Miramistin v kompleksnoy programme bor'by s gospital'noy infektsiyey v khirurgicheskom statsionare//V sb.: Miramistin: primeneniye v khirurgii, travmatologii i kombustiologii. M*—2006.—S. 27-33. Makeyeva I. M Ye. V. Borovskiy, M V. Matavkina, Ye. A. Brovenko. *Primeneniye preparata Miramistin v kompleksnom lechenii zabolevaniy slizistoy obolochki rta. Farmateka.*—2013.—No 3—S.11 Blatun L. A. *Miramistin in the complex program of control of hospital infection in a surgical hospital//In report: Miramistin: application in surgery, traumatology and combustiology. M*—2006.—P. 27-33.; Makeeva I. M. E. V. Borovsky, M V. Matavkina, E. A. Brovenko. *Application of the drug Miramistin in the complex treatment of diseases of the oral mucosa. Pharmacy.*—2013.—No 3—P.1].

Fluomysin (dequalinium chloride) is a broad-spectrum antiseptic, active against most gram-positive bacteria *Streptococcus* spp., *Staphylococcus aureus, Listeria* spp., anaerobs *Peptostreptococcus* (group D), fungi of the genus *Candida (Candida tropicalis, Candida* aMXicans, *Candida glabrata*), gram-negative bacteria *Gardnerella vaginalis, Escherichia coli, Serratia* spp., *Klebsiella* spp., *Pseudomo-* nas spp., *Proteus* spp., and protozoa (*Trichomonas vaginalis*). It is used in bacterial vaginosis, candidiasis of the skin, nail walls, oral mucosa, inflammatory processes in the oral cavity and pharynx (tonsillitis, stomatitis, including aphthose, glossitis, etc.). pharyngitis) [*Spravochnik Vidal' «Lekarstvennyye preparaty v Rossii».Vidal Handbook "Medicines in Russia"*. https://www.vidal.ru/drugs/fluomisin_22520].

Benzalkonium chloride (alkyldimethyl(phenylmethyl) ammonium chloride) is an antiseptic active against gram-positive (*Staphylococcus* spp., *Streptococcus* spp., *Streptococcus pneumoniae*, etc.), gram-negative (*Pseudomonas aeruginosa, Escherichia coli, Klebsiella* spp. etc.) and anaerobic bacteria, fungi and mold. It is used in primary and primary-delayed treatment of wounds, prevention of secondary infection of wounds by hospital strains of microorganisms, bacterial vaginosis, drainage of bone cavities after surgery in osteomyelitis [*Spravochnik Vidal' «Lekarstvennyye preparaty v Rossii». Vidal Handbook "Medicines in Russia"*. https://www.vidal.ru/drugs/dettol_benzalkonium_chloride_30527].

It should be noted that the medicines described above, in the opinion of the applicant, cannot be considered as analogues to the claimed invention due to the fact that they do not coincide with the claimed compound by chemical structure, although they have antibacterial, antimycotic, antiviral and antiprotozoic activity (coincide for purpose) comparable to the declared invention in greater or less degree.

BRIEF DESCRIPTION OF THE DRAWINGS

The claimed technical solution is illustrated by FIGS. 1,2 and sixteen (16) tables shown in the description text (to improve understanding of the application text by the expert).

SUMMARY OF THE INVENTION

Figure 1:
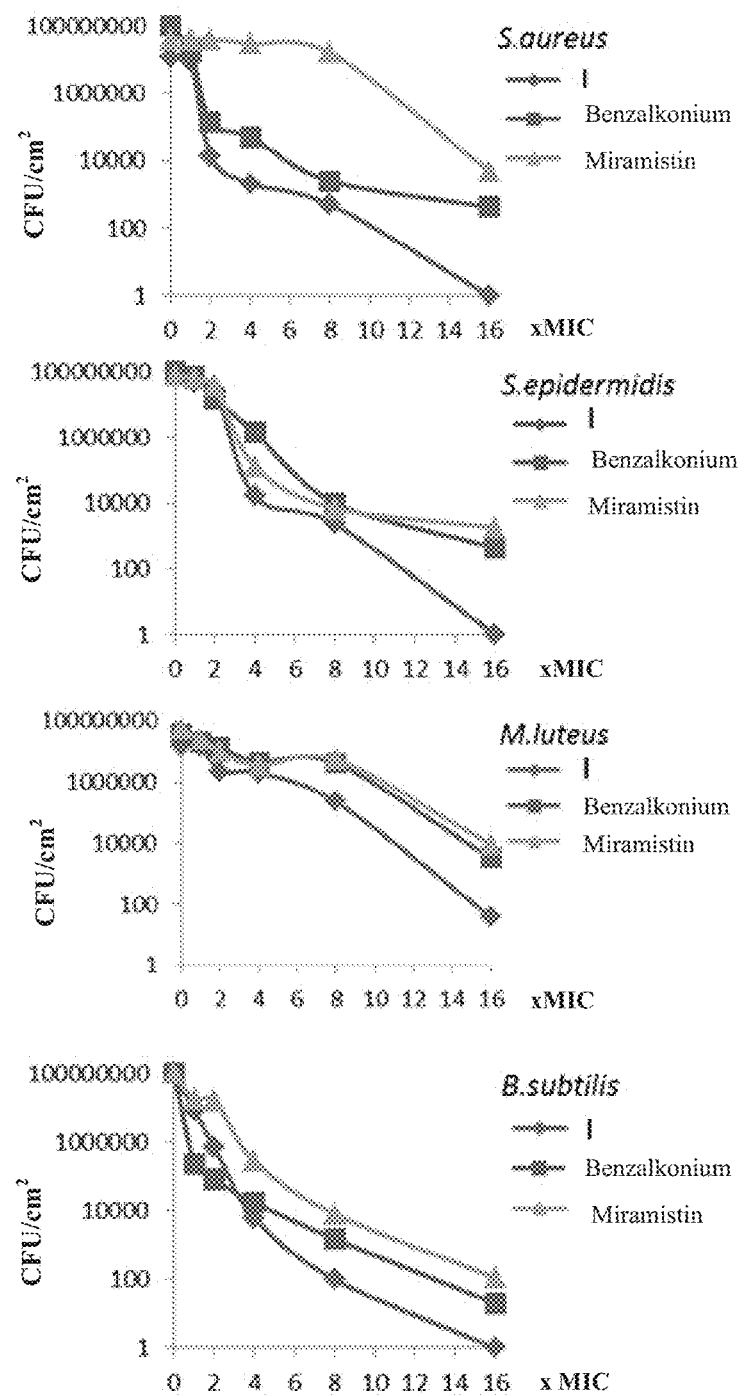
FIG. 1 presents a comparative analysis of antibacterial activity of compound I, benzalconium chloride and miramistin against cells of gram-positive bacteria immersed in a biofilm matrix.

The objective of the invention is a new compound with high antibacterial, antimycotic, antiviral and antiprotozoal activity comparable with existing antiseptics, but significantly less toxic.

The technical result of the claimed invention is to obtain a new compound of formula I, which contains both a fragment of a natural compound (vitamin $B_6$) and a quaternary ammonium fragment.

The problem is solved, and the specified technical result is achieved by obtaining the claimed new derivative of vitamin $B_6$ of formula I:

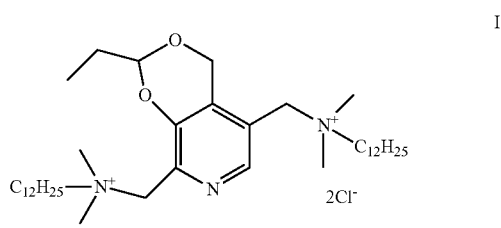

according to the following diagram 1, where the claimed compound is indicated by the number I.

Diagram 1

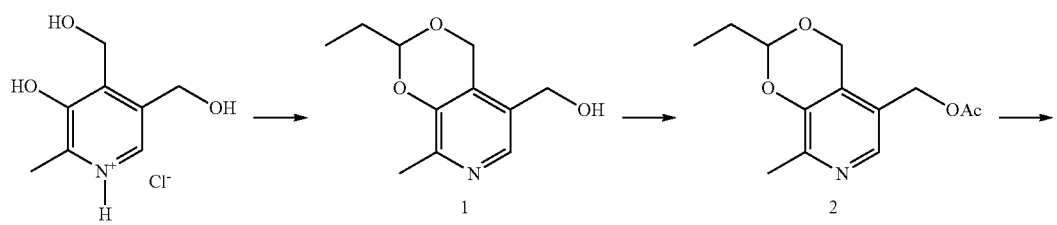

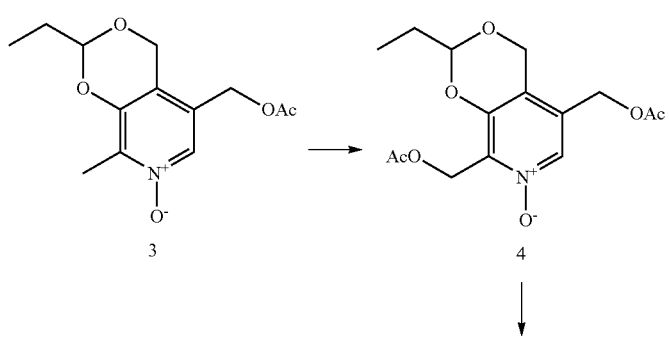

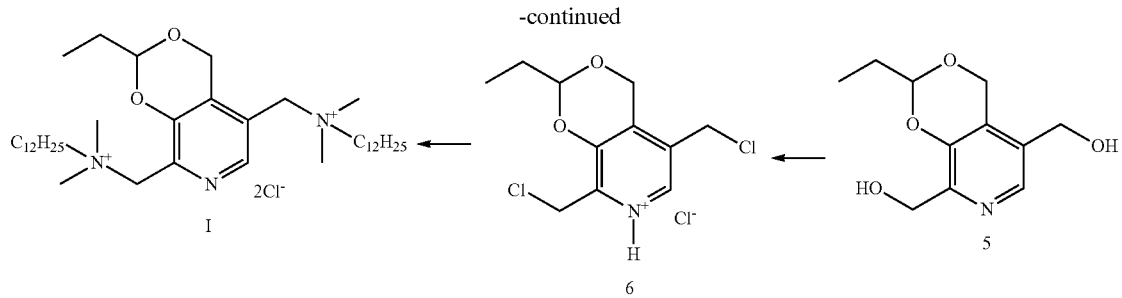

The characteristics of the new compound are given below in the examples of specific performance. The structure of the obtained compound was confirmed by mass spectrometry, $^1$H and $^{13}$C NMR spectroscopy. NMR spectra were recorded on the AVANCE-400 device (Bruker, Germany). The chemical shift was determined with respect to the signals of residual protons of deuterated solvents ($^1$H and $^{13}$C). Melting temperatures were determined using Stanford Research Systems MPA-100 OptiMelt. Control over the course of reactions and purity of compounds was carried out by TLC method on Sorbfil Plates. High-resolution mass spectra (FIRMS) experiment was carried out using TripleTOF 5600, AB Sciex (Germany) mass spectrometer from methanol solution by ionization—turboion spray (TIS)—at energy of impacts with nitrogen molecules equal to 10 eV.

DETAILED DESCRIPTION OF THE PREFERRED EMBODIMENTS

Example 1. Preparation of 5,8-(Bis(methylene (N, N-dimethyl-N-dodecylammonium))-2-ethyl-4H-[1, 3] dioxino [4,5-c] pyridinium dichloride (I)

Phase 1. Preparation of 5-(hydroxymethyl)-2-ethyl-8-methyl-4H-[1,3] dioxino[4,5-c] pyridine (1)

28.1 g (146.0 mmol) of p-toluenesulfonic acid monohydrate were boiled with a Dean-Stark apparatus in 500 ml of toluene for 2 hours. The solution was then cooled to room temperature and 30.0 g (146.0 mmol) of pyridoxine hydrochloride and 15.0 ml (209.5 mmol) of propionic aldehyde were added. The reaction mixture was boiled for 8 hours with a Dean-Stark apparatus. Then the solvent was driven away in vacuum. A solution of 18.0 g (450.0 mmol) of sodium hydroxide in 100 ml of water was added to the precipitate while stirring. Next, the aqueous portion was washed with 500 ml of chloroform, the organic portion was separated, dried in vacuo and recrystallized from 100 ml of toluene. Yield was 17.0 g (56%) of colorless crystalline substance, with melting point equal to 111-112° C.

NMR spectrum $^1$H (400 MHz, DMSO-d$_6$) δ, ppm: 1.00 t (3H, $^3J_{H-H}$=7.5 Hz, CH$_3$CH$_2$), 1.77-1.83 sq d (2H, $^3J_{H-H}$=7.5 Hz, $^3J_{H-H}$=5.0 Hz, CH$_3$CH$_2$), 2.30 s (3H, CH$_3$), 4.38 d (2H, $^3J_{H-H}$=4.3 Hz, CH$_2$OH), 4.95 s (2H, CH$_2$O), 5.06 t (1H, $^3J_{H-H}$=5.0 Hz, CHC$_2$H$_5$), 5.18 t (1H, $^3J_{H-H}$=4.3 Hz, CH$_2$OH), 7.93 s (1H, CH$_{pyr}$).

NMR spectrum $^{13}$C (100 MHz, DMSO-d$_6$) δ, ppm: 7.78 s (CH$_3$CH$_2$), 18.16 s (CH$_3$), 27.06 s (CH$_3$CH$_2$), 58.21 s (CH$_2$O), 63.43 s (CH$_2$O), 100.02 s (CHC$_2$H$_5$), 126.88 s (S$_{pyr}$), 130.94 s (C$_{pyr}$), 138.95 s (CH$_{pyr}$), 145.09 s (C$_{pyr}$), 146.91 s (C$_{pyr}$).

Mass Spectrum (HRMS-ESI): Found [M+H]$^+$ 210.1125, C$_{11}$H$_{16}$NO$_3$. Calculated [M+H]$^+$ 210.1130.

Phase 2. Preparation of 5-(acetoxymethyl)-2-ethyl-8-methyl-4H-[1,3] dioxino[4,5-c] pyridine (2)

To a solution of 10.0 g (47.8 mmol) of compound 1, 7.64 ml (55.1 mmol) of triethylamine in 150 ml of dichloromethane when stirred, a solution of 3.74 ml (52.6 mmol) of acetyl chloride in 30 ml of dichloromethane was added dropwise over 20 minutes. The resulting solution was stirred at room temperature for 3 hours. The reaction mixture was washed successively with 200 ml of 5% sodium bicarbonate solution and 100 ml of water. The organic part was separated and dried in a vacuum. Yield is 12.0 g (quantitative), colorless oily substance.

NMR spectrum $^1$H (400 MHz, CDCl$_3$) δ, ppm: 1.08 t (3H, $^3J_{H-H}$=7.5 Hz, CH$_3$CH$_2$), 1.89-1.93 m (2H, CH$_3$CH$_2$), 2.07 s (3H, CH$_3$), 2.44 s (3H, CH$_3$), 4.91, 4.95 AB system (2H, $^3J_{H-H}$=16.0 Hz, CH$_2$), 4.97 s (2H, CH$_2$), 4.97 t (1H, $^3J_{H-H}$=5.0 Hz, CHC$_2$H$_5$), 8.04 s (1H, CH$_{pyr}$).

NMR spectrum $^{13}$C (100 MHz, CDCl$_3$) δ, ppm: 7.94 s (CH$_3$CH$_2$), 18.42 s (CH$_3$), 20.91 s (CH$_3$), 27.64 s (CH$_3$CH$_2$), 61.16 s (CH$_2$O), 64.07 s (CH$_2$O), 100.95 s (CHC$_2$H$_5$), 124.85 s (C$_{pyr}$), 127.75 s (C$_{pyr}$), 140.78 s (CH$_{pyr}$), 147.95 s (C$_{pyr}$), 148.34 s (C$_{pyr}$), 170.58 s (C(O)).

Phase 3. Preparation of 5-(acetoxymethyl)-2-ethyl-8-methyl-4H-[1,3] dioxino[4,5-c] pyridine N-oxide (3)

To a solution of 12.0 g (47.8 mmol) of compound 2 in 300 ml of dichloromethane was added 19.2 g (66.8 mmol) of 60% m-chloroperbenzoic acid and stirred without light at room temperature for 24 hours. Then the reaction mixture was consecutively washed with 10% sodium sulfite solution (2*150 ml), 5% sodium bicarbonate solution (2*150 ml) and water (75 ml). The organic layer was separated and the solvent was removed in vacuum. Product yield is 11.91 g (93%), colorless crystals.

NMR spectrum $^1$H (400 MHz, CDCl$_3$) δ, ppm: 1.07 t (3H, $^3J_{H-H}$=7.5 Hz, CH$_3$CH$_2$), 1.89-1.93 m (2H, CH$_3$CH$_2$), 2.10 s (31-1, CH$_3$), 2.41 s (31-1, CH$_3$), 4.88 s (211, CH$_2$), 4.89 s (2H, CH$_2$), 4.99 t (1H, $^3J_{H-H}$=5.0 Hz, CHC$_2$H$_5$), 7.98 s (1H, CH$_{pyr}$).

NMR spectrum $^{13}$C (100 MHz, CDCl$_3$) δ, ppm: 7.75 s (CH$_3$CH$_2$), 10.21 s (CH$_3$), 20.71 s (CH$_3$), 27.41 s (CH$_3$CH$_2$), 59.88 s (CH$_2$O), 63.76 s (CH$_2$O), 101.50 s (CHC$_2$H$_5$), 117.89 s (C$_{pyr}$), 126.71 s (C$_{pyr}$), 132.06 S (CH$_{pyr}$), 139.29 S (C$_{pyr}$), 149.52 s (C$_{pyr}$), 170.16 s (C(O)).

Phase 4. Preparation of 5.8 bis(acetoxymethyl)-2-ethyl-4H-[1.3] dioxino [4.5-c] pyridine (4)

A solution of 11.9 g (44.6 mmol) of compound 3 in 40 ml (424 mmol) of acetic anhydride and 60 ml of dichloromethane was heated for 6 hours at 50° C. The solvent was then removed in vacuum and the remaining oil was dissolved in dichloromethane. The resulting solution was consecutively washed with 5% sodium bicarbonate solution (150 ml) and water (100 ml). The organic layer was separated and the solvent was removed in vacuum. The product was used in the next step without further purification. Product yield is 13.5 g (97%), black oil-like substance.

Phase 5: Preparation of 5,8-bis(hydroxymethyl)-2-ethyl-4H-[1,3] dioxino [4,5-c] pyridine (5)

13.5 g (43.7 mmol) of compound 4 was dissolved in 140 ml of ethanol. To the obtained mixture was added a solution of 3.48 g (87.0 mmol) of sodium hydroxide in 30 ml of water. The solution was stirred for 1 hour at 50° C., acidified with hydrochloric acid to pH=6.5 and the solvent was distilled off in vacuo. 150 ml of water was poured into the dry residue and boiled for 15 minutes. The insoluble resinous precipitate was filtered off at 80° C., and the solvent was concentrated to 80 ml and left in refrigerator for 12 hours. The precipitate was filtered off. Product yield is 3.7 g (38%), brown crystalline substance.

NMR spectrum $^1$H (400 MHz, DMSO-d$_6$) δ, ppm: 1.00 t (3H, $^3J_{H-H}$=7.5 Hz, C$\underline{H_3}$CH$_2$), 1.78-1.82 m (2H, CH$_3$C$\underline{H_2}$), 4.42 d (2H, =4.2 Hz, C$\underline{H_2}$OH), 4.48 d (2H, =5.6 Hz, C$\underline{H_2}$OH), 4.86 t (1H, $^3J_{H-H}$=5.6 Hz, CH$_2$O$\underline{H}$), 4.97 s (2H, CH$_2$), 5.07 t (1H, $^3J_{H-H}$=5.0 Hz, CH$_2$O$\underline{H}$), 5.23 t (1H, $^3J_{H-H}$=4.8 Hz, C$\underline{H}$C$_2$H$_5$), 8.04 s (1H, CH$_{pyr}$).

NMR spectrum $^{13}$C (100 MHz, DMSO-d$_6$) δ, ppm: 7.68 s ($\underline{C}$H$_3$CH$_2$), 26.94 s (CH$_3$$\underline{C}$H$_2$), 58.14 s (CH$_2$), 59.02 s (CH$_2$), 63.44 s (CH$_2$), 100.02 s ($\underline{C}$HC$_2$H$_5$), 127.37 s (C$_{pyr}$), 132.24 s (CH$_{pyr}$), 138.68 s (C$_{pyr}$), 146.52 s (C$_{pyr}$), 146.94 s (C$_{pyr}$).

Phase 6: Preparation of 5.8 bis(chloromethyl)-2-ethyl-4H-[1.3] dioxino [4.5-c] pyridinium chloride (6)

To a suspension of 3.7 g (16.4 mmol) of substance 5 in 40 ml of toluene was added dropwise 5.0 ml (68.9 mmol) of thionyl chloride. The reaction mixture was stirred at 70° C. for 2 hours. 50 ml of diethyl ether was added to the mixture and the precipitate was filtered off. Product yield is 4.66 g (95%), yellow crystalline substance.

Phase 7: Preparation of 5,8-(Bis(methylene (N, N-dimethyl-N-dodecylammonium))-2-ethyl-4H-[1, 3] dioxino [4,5-c] pyridinium dichloride (I)

To a solution of 1.1 g (13.1 mmol) of sodium bicarbonate in 40 ml of water, 3.8 g (12.7 mmol) of compound 6 was added while stirring. The resulting precipitate was filtered off and dried in vacuo. The resulting 2.9 g (11.1 mmol) of product (88% yield) were dissolved in 50 ml of ethanol and 5.98 ml (22.2 mmol) of N, N-dimethyldodecylamine were added. The reaction mixture was stirred at 70° C. for 8 hours. The solvent was distilled off in a vacuum. The resulting precipitation was boiled in 120 ml of acetone. After cooling to room temperature, the precipitation was filtered off and dried in vacuo. Yield is 5.64 g (74%), white crystalline substance.

NMR spectrum $^1$H (400 MHz, CDCl$_3$) δ, ppm: 0.84 t (6H, $^3J_{HH}$=6.7 Hz, 2C$\underline{H_3}$C$_{11}$H$_{22}$), 1.00 t (3H, $^3J_{H-H}$=7.5 Hz, C$\underline{H_3}$CH$_2$), 1.22-1.33 m (32H, 16CH$_2$), 1.70-1.84 m (6H, 3CH$_2$), 2.96 m (2H, CH$_2$), 3.29-3.32 m (12H, 4CH$_3$N$^+$), 3.50-3.83 m (4H, 2CH$_2$N$^+$), 4.69, 4.74 (AB-system, 2H, $^2J_{HH}$=-13.6 Hz, CH$_2$), 5.10, 5.55 (AB-system, 2H, $^2J_{HH}$=-16.7 Hz, CH$_2$), 5.11, 5.21 (AB-system, 2H, $^2J_{HH}$=-13.6 Hz, CH$_2$), 8.60 s (1H, CH$_{pyr}$).

NMR spectrum $^{13}$C (100 MHz, CDCl$_3$) δ, ppm: 8.01 s (CH$_3$), 14.21 s (CH$_3$), 22.77 s (CH$_3$), 23.18 s (CH$_2$), 26.46 s (CH$_2$), 27.57 s (CH$_2$), 29.43 s (CH$_2$), 29.46 s (CH$_2$), 29.53 s (CH$_2$), 29.62 s (CH$_2$), 29.70 (s, CH$_2$), 31.99 s (CH$_2$), 49.60 s (CH$_3$N$^+$), 49.76 s (CH$_3$N$^+$), 51.11 s (CH$_3$N$^+$), 51.34 s (CH$_3$N$^+$), 61.94 s (CH$_2$), s 62.26 (CH$_2$), 65.60 s (CH$_2$), 65.66 s (CH$_2$N$^+$), 66.34 s (CH$_2$N$^+$), 102.04 s ($\underline{C}$(CH$_3$)$_2$), 122.92 s (C$_{pyr}$), 134.60 s (C$_{pyr}$), 136.87 s (C$_{pyr}$), 146.54 s (C$_{pyr}$), 150.88 s (C$_{pyr}$).

Example 2. In Vitro Study of the Antibacterial Activity of Quaternary Ammonium Salt I A comparative assessment of the spectrum of antibacterial action was carried out on archival and clinical strains of gram-positive and gram-negative microorganisms in accordance with the [*Opredeleniye chuvstvitel'nosti mikroorganizmov k antibakterial'nym preparatam (Metodicheskiye ukazaniya MUK 4.2.1890-04). Utverzhdeny i vvedeny v deystviye Glavnym gosudarstvennym sanitarnym vrachom Rossiyskoy Federatsii G. G. Onishchenko 04.03.2004 g. Determination of the sensitivity of microorganisms to antibacterial drugs (Guidelines MUK 4.2.1890-04). Approved and put into effect by the Chief State Sanitary Doctor of the Russian Federation G. G. Onishchenko on* 4 Mar. 2004].

The value of the minimum inhibitory concentration (MIC) was determined by the method of serial dilutions on Müller-Hinton broth using 96-well sterile plates. Two-fold dilutions of the test substances in a nutrient medium were prepared. The final concentrations were 1-128 ug/ml. The growth of cultures was assessed visually, comparing the growth of microorganisms in the presence of test compounds with the growth of culture without them. The presence of microorganism growth in the broth (turbidity of the broth) indicates that this concentration of the studied drug is insufficient to suppress its viability. The first lowest concentration of the studied substance (from a series of consecutive dilutions), where bacterial growth is not visually determined, is considered to be the minimum inhibitory concentration (MIC). MIC was determined by the method of serial dilutions in broth with increment=2, so the differences of neighboring dilutions are not considered to be significant. In each experience there is a positive (broth with growing culture) and a negative (broth without growing culture) control.

To determine the MIC, 10 μl of culture medium was taken from those wells in which growth was not observed, and inoculation was performed on a dense Müller-Hinton broth. For the preparation of the inoculum, a pure, daily culture of gram-positive and gram-negative microorganisms grown on a dense nutrient medium was used. Nutrient medium is Müller-Hinton broth, which was prepared from dry media (Müller-Hinton broth, Acumedia, Baltimore), cultivation was carried out on agarized Müller-Hinton broth, including an additional 2% agar. The media were autoclaved at 121° C. for 15 minutes. In a sterile isotonic solution of sodium chloride, a suspension of microorganisms was prepared, adjusting the inoculum density to 0.5 according to the McFarland standard (1.5·10$^8$ CFU/ml). Then, the resulting inoculum was diluted to a concentration of 10$^7$ CFU/ml with Müller-Hinton broth. The inoculum was used within 15 minutes after preparation; the purity of the bacterial strains was monitored before each experiment.

100 μl of Müller-Hinton broth was added to the wells of each plate; The tested substance was introduced into the first well at a concentration of 128 µg/ml in a volume of 100 µl and its concentration was adjusted to 0.5 µg/ml by consecutive two-fold dilution. Then, the prepared inoculum (100 µl) was added to each well, thereby diluting twice the concentration of the studied compounds. As a control, wells that did not contain the tested substances were included (control of the growth of the culture). In addition, the purity of nutrient media and solvents was monitored. The plates were incubated in a thermostat at 37° C. for 24 hours. The growth of cultures was assessed visually, comparing the growth of microorganisms in the presence of test compounds with the growth of culture without them.

For the MIC was taken the minimum concentration of the studied compounds, providing complete suppression of the visible growth of the studied strains of microorganisms. The maximum value obtained in three independent experiments was taken as the MIC of the compound.

As a result of the screening of the antibacterial activity of compound I, it was found that the MIC for clinical staphylococci is 1-8 µg/ml, and in only one case is 16 µg/ml (S. aureus 967 MRSA strain), for clinical enterococci MIC is within 0.03-4 µg. These values are comparable with the indicators found for benzalkonium chloride, and on average are (2-4) times better than the indicators of miramistin (table 1).

With respect to gram-negative bacteria, the drug was less active, MIC in 11 strains was 2-4 µg/ml, 8-16 µg/ml in 18 strains, 32-64 µg/ml in 12 strains. The tested new drug was comparable in activity with benzalkonium chloride, and in some strains exceeded it (especially in the case of Ps. Aeruginosa strains). Compound I was much more active compared to miramistin, in which the MIC is in the range of 32-64 µg/ml, with the exception for the archival strain E. coli ATCC 25922.

TABLE 1

The mean values of the MIC for compound I and the comparator drugs in relation to gram-positive and gram-negative microorganisms (in µg/ml), when the concentration of inoculum is $10^7$ CFU/ml

| Seq No. | Strain | I | Benzalconium chloride | Miramistin |
|---|---|---|---|---|
| Gram-positive | | | | |
| 1 | S. aureus ATCC 29213 | 4 | 2 | 16 |
| 2 | S. epidermidis 15990 | 4 | 1 | 8 |
| 3 | B. subtilis 168 | 2 | 0.5 | 2 |
| 4 | S. haemoliticus 837 MRSA | 8 | 16 | 64 |
| 5 | S. aureus 967 MRSA | 16 | 8 | 16 |
| 6 | S. aureus 981 MRSA | 4 | 4 | 4 |
| 7 | S. aureus 983 MRSA | 8 | 4 | 4 |
| 8 | S. aureus 1053 MRSA | 2 | 4 | 4 |
| 9 | S. intermedius 1061 MRSI | 1 | 4 | 8 |
| 10 | S. aureus 1065 MRSA | 2 | 4 | 8 |
| 11 | S. aureus 1130 MRSA | 2 | 2 | 4 |
| 12 | S. aureus 1131 MRSA | 2 | 2 | 4 |
| 13 | S. aureus 1134 MRSA | 2 | 2 | 8 |
| 14 | S. intermedius 1143 MRSA | 4 | 4 | 8 |
| 15 | S. aureus 1145 MRSA | 2 | 2 | 8 |
| 16 | S. aureus 1163 MRSA | 4 | 4 | 4 |
| 17 | S. aureus 1167 MRSA | 4 | 2 | 4 |
| 18 | S. aureus 1168 MRSA | 1 | 2 | 8 |
| 19 | S. aureus 1173 MRSA | 2 | 8 | 16 |
| 20 | S. aureus 2020 MRSA | 4 | 4 | 8 |
| 21 | S. aureus 18 | 4 | <0.5 | 16 |
| 22 | S. aureus 19 | 2 | <0.5 | 16 |
| 23 | S. aureus 20 | 4 | <0.5 | 32 |
| 24 | S. aureus 21 | 1 | <0.5 | 16 |
| 25 | S. aureus 22 | 1 | <0.5 | 8 |
| 26 | E. faecalis 23 | 0.03 | <0.5 | 4 |
| 27 | E. faecium 24 | 0.03 | <0.5 | 16 |
| 28 | E. faecium 25 | 0.03 | <0.5 | <0.5 |
| 29 | E. faecalis 26 | 1 | 0.5 | 4 |
| 30 | E. faecium 27 | 0.03 | 0.5 | 32 |
| 31 | E. faecium 28 | 0.03 | <0.5 | 32 |
| 32 | E. faecium 29 | 0.03 | <0.5 | 8 |
| 33 | E. faecium 30 | 0.03 | <0.5 | <0.5 |
| 34 | E. faecium 31 | 0.03 | <0.5 | 4 |
| 35 | E. faecium 32 | 0.03 | <0.5 | <0.5 |
| 36 | E. faecium 3028 | 1 | 4 | 16 |
| 37 | E. faecium 3030 | 1 | 0.5 | 0.5 |
| 38 | E. faecalis 3047 | 4 | 2 | 2 |
| 39 | E. faecalis 3051 | 4 | 2 | 2 |
| 40 | E. faecalis 3060 | 1 | 4 | 8 |
| 41 | E. faecium 3062 | 0.5 | 1 | 0.5 |
| 42 | E. faecium 4402 | 0.06 | 1 | 4 |
| 43 | E. faecium 4403 | 0.03 | 2 | 64 |
| 44 | S. aureus 1053a | 2 | 1 | 4-8 |
| 45 | M. luteus | 2 | 1 | 2 |
| 46 | S. aureus ATCC 209p | 2 | 4 | 8 |
| Gram-negative | | | | |
| 47 | E.coli ATCC 25922 | 2 | 1 | 4 |
| 48 | Kl. pneumoniae | 2 | >64 | >64 |
| 49 | Ps. aeruginosa ATTC 27853 | 4 | >64 | >64 |
| 50 | Moraxella sp. 713 | 8 | 4 | 32 |
| 51 | Moraxella sp. 723 | 4 | 4 | 32 |
| 52 | Moraxella sp. 764 | 8 | 4 | 64 |
| 53 | Moraxella sp. 765 | 4 | 32 | 64 |
| 54 | Moraxella sp.829 | 4 | 32 | 32 |
| 55 | Moraxella sp.834 | 4 | 2 | 32 |
| 56 | Acinetobacter spp. 1 | 16 | >64 | 64 |
| 57 | Acinetobacter spp. 3 | 8 | 4 | 64 |
| 58 | Acinetobacter spp. 4 | 8 | 4 | >64 |
| 59 | Pseudomonas spp. 5 | 8 | 32 | >64 |
| 60 | Pseudomonas spp.6 | 16 | 16 | >64 |
| 61 | Stenotrophomonas spp. 9 | 8 | 4 | 64 |
| 62 | Klebsiella spp. 10 | 8 | 1 | 64 |
| 63 | Klebsiella spp. 11 | 16 | 2 | 64 |
| 64 | Klebsiella spp. 12 | 16 | 2 | >64 |
| 65 | E. coli 13 | 8 | 2 | 32 |
| 66 | Serratia spp. 15 | 16 | 2 | >64 |
| 67 | Enterobacter spp. 16 | 8 | 4 | 64 |
| 68 | Proteus spp. 17 | 64 | 16 | >64 |
| 69 | Kl. pneumoniae 645 PR | 32 | 16 | 64 |
| 70 | Ps. aeruginosa 1202 | 32 | >64 | >64 |
| 71 | Kl. pneumoniae 1342 PR | 32 | 32 | 64 |
| 72 | A. baumannii 1425 PR | 8 | 32 | 64 |
| 73 | Kl. pneumoniae 1435 PR | 32 | 32 | 64 |
| 74 | A. baumannii 1440 | 8 | 32 | 64 |
| 75 | E. coli 1440 | 32 | 32 | 64 |
| 76 | Kl. pneumoniae 1766 | 16 | 16 | 64 |
| 77 | Kl. pneumoniae 1781 | 2 | 16 | 64 |
| 78 | Kl. pneumoniae 1812 PR | 64 | 64 | 64 |
| 79 | Ps. aeruginosa 1913 PR | 64 | >64 | >64 |
| 80 | Ps. aeruginosa 1945 PR | 64 | >64 | >64 |
| 81 | Kl. pneumoniae 1953 PR | 2 | 16 | 64 |
| 82 | Ps. aeruginosa 1959 | 32 | >64 | 64 |
| 83 | S. marcescens 1966 PR | 32 | 64 | 64 |
| 84 | Ps. aeruginosa 2869 | 32 | 64 | 64 |
| 85 | E. coli MG 1655 | 2 | 2 | 8 |
| 86 | S. marcescens | 4 | 2 | 32 |
| 87 | E. coli CDCF-50 | 8 | 4 | 64 |

It should be noted that all bacterial strains ($MIC_{100}$<64 ug/ml) were sensitive to compound I, while miramistin's $MIC_{89}$<64 ug/ml and benzalkonium chloride $MIC_{92}$<64 ug/ml.

Example 3. Determination of the Antibacterial Activity of Compound I Against Cells Immersed in a Biofilm Matrix To determine the effectiveness of the antibiotic against bacteria in the cell, bacteria were grown in Basal medium for 3 days at a temperature of 37° C. without swinging to obtain a dense biofilm [A. R Kayumov, Khakimullina E., Sharafutdinov I, Trizna E., Latypova L., Lien Thi, Margulis A., Bogachev M, Kurbangalieva A. *Inhibition of biofilm formation in Bacillus subtilis by new halogenated furanoses. J. Antibiotics.*—2014.—V. 68.—No 5.—P. 297-301.]. Then the biofilm was washed with a sterile 0.9% NaCl solution and fresh sterile medium was poured. Antiseptics were added to concentrations (1-16)×MBC (minimum bactericidal concentration) and incubated for 24 hours. Then the culture fluid was removed from the wells, washed once with 0.9% NaCl solution to remove non-adherent cells, and cell viability in biofilms was evaluated by counting CFU by Drop plate analysis [B. Herigstad, M Hamilton, J. Heersink *How to optimize the drop plate method for enumerating bacteria. J Microbiol Methods.*—2001.—V. 44.—P. 121-129]. To do this, the biofilm was mechanically removed from the surface and homogenized in 0.9% NaCl by pipetting and ultrasonic treatment. Then, serial 10-fold dilutions of the bacterial suspension in 0.9% NaCl were prepared, and 5 µl of each suspension were transferred to plates with dense nutrient medium. CFU was counted from drops containing 5-10 colonies.

Figure 2:
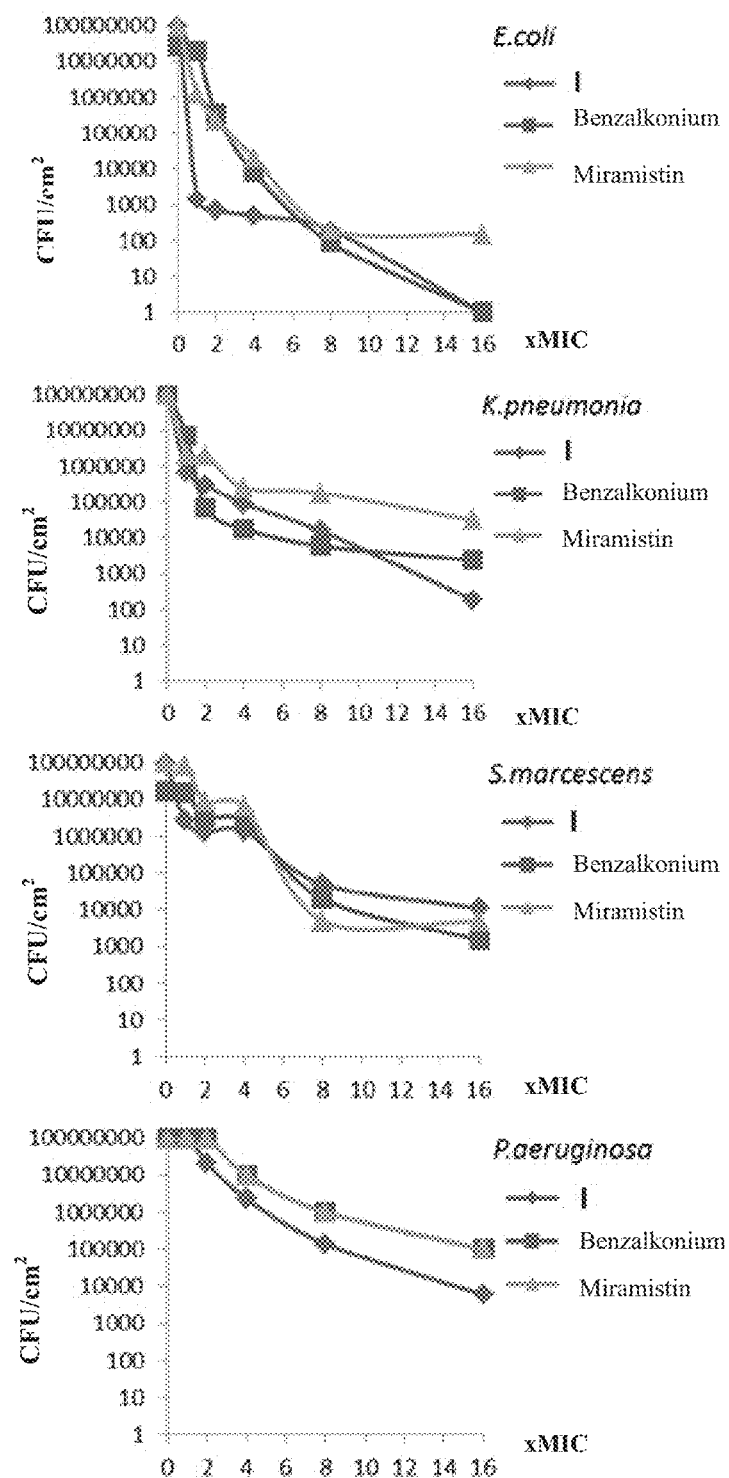
FIG. 2 presents a comparative analysis of antibacterial activity of compound I, benzalconium chloride and miramistin against cells of gram-negative bacteria immersed in a biofilm matrix.

The results of the study of antimicrobial activity against cells of the studied strains immersed in the biofilm matrix, in comparison with miramistin and benzalkonium chloride, are presented in FIGS. 1 and 2.

With respect to gram-positive microorganisms in the biofilm, compound I showed a 2-fold higher activity compared to miramistin and benzalkonium chloride: the same decrease in the number of CFU occurred at a twice lower excess of MBC in compound I compared with miramistin and benzalkonium chloride. At the same time, miramistin was 2 times less active than benzalkonium chloride.

For gram-negative microorganisms in the biofilm, compound I showed the same activity as miramistine and benzalconium chloride against *K. pneumonia, S.marcescens, E. coli*. As for the strain *P.aeruginosa*, the activity of compound I is significantly higher than that of comparison antiseptics. A decrease in the number of CFU by 3 orders of magnitude occurred when MBC was exceeded by 4-8 times for compound I and 16 times for miramistin and benzalkonium chloride, which is an undoubted advantage of the developed antiseptic.

Example 4. In Vitro Study of the Antiviral Activity of Compound I

The study of the antiviral activity of compound I in vitro was carried out in accordance with [D. L. Kuznetsov, A. YA. Samuylenko, V. I. Belousov *Immunofermentnaya diagnostika IRT KRS. Veterinariya.*—2002.—No 3.—S. 22-25. D. L. Kuznetsov, A. Y.6 Samuylenko, V. I. Belousov *Enzyme-linked immunosorbent assay for cattle IBR. Veterinary medicine.*—2002.—No 3.—P. 22-25].

Cells of a light cow embryo (LCE) are obtained from the Federal State Budgetary Institution "All-Russian Institute of Experimental Veterinary Medicine", Moscow. Bovine rhinotracheitis virus (herpes virus family), vaccine strain "TK-A (VIEV)-V2" was obtained from the Federal State Budgetary Institution "All-Russian Institute of Experimental Veterinary Medicine", Moscow.

Evaluation of the antiviral activity of compound I was carried out in an appropriate medium on LCE cells that were infected with the IBR virus belonging to the type 1 herpes virus family.

The virus was incubated in the presence of compound I in a culture medium at 37° C. for one hour at various concentrations; miramistin and benzalkonium chloride served as control preparations. After incubation of the virus with substances, it was added to the cell culture, which was then incubated at 37° C., 5% $CO_2$ for 72 hours.

Evaluation of the cytopathogenic effect was carried out visually by the state of the cell monolayer as compared with the controls (virus without incubation with the drug, the studied drug concentrations without the virus). The virus titer was calculated using the method of Reed-Muench in the modification of Ashmarin and expressed in Ig $TCD_{50}$/ml.

As a result of studies on antiviral activity of compound I it was revealed that the substance has a virulicidal effect against herpes virus type 1 with an infectious titer 6.0 Ig $TCD_{50}$/ml (Table 2). Virulicidal effect of compound I is slightly weaker (200 ug/ml) than in miramistin (150 ug/ml) and comparable to the effects of benzalconium chloride.

TABLE 2

The results of a study of antiviral activity of drugs

| The drug | Concentration, µg/ml | | | | |
|---|---|---|---|---|---|
| | 0 | 50 | 100 | 150 | 200 |
| Miramistin | – | – | – | – | – |
| Miramistin with the virus | ++++ | ++++ | +++ | – | – |
| Benzalconium chloride | – | – | – | – | – |
| Benzalconium chloride with the virus | ++++ | ++++ | ++++ | ++ | – |
| Compound I | – | – | – | – | – |
| Compound I with the virus | ++++ | ++++ | ++++ | ++ | – |

Where:
++++ - 90-100% destruction of the monolayer;
+++ - –70-90% destruction of the monolayer;
++ - –40-70% destruction of the monolayer;
+ 10-40% destruction of the monolayer;
–0-10% destruction of the monolayer.

Example 5. Determination of the Antiprotozoic Activity of the Compound I In Vitro Evaluation of the antiprotozoal activity of compound I was determined by the viability of the protozoa genus of hypotrichs *Stylonychia mytilus* in a nutrient medium in the presence of the studied substances. A mother liquor of compound I (10 mg/ml) was prepared in a mixture of DMSO and 96% ethanol (1:1). A 1% aqueous solution of DMSO and ethyl alcohol served as a negative control, and miramistin, benzalkonium chloride, and chlorhexidine were used as reference preparations. Then, from the mother liquors by repeated dilutions with water, working solutions were prepared corresponding to doses of 5; 10; 20; 25; 50; 75; 100 and 150 µg/ml. 10 µl of culture medium with protozoa and 10 µl of a solution of the test substance were applied to a chamber slide. The experiment was done in five replicates.

Slides were examined under a light microscope, antiprotozoal activity of substances (MIC and $IC_{50}$) were determined by the death of protozoa. The Hill regression model with 5 parameters was used for the analysis.

As a result of the studies, it was found that compound I has a pronounced antiprotozoal effect against Stylonychia mytilus (table 3). The antiprotozoal effect of compound I against the hypotrichs (Stylonychia mytilus) was comparable (25 µg/ml) with chlorhexidine (20 µg/ml), benzalkonium chloride (30 µg/ml) and was superior to miramistin (50 µg/ml).

TABLE 3

The results of a study of antiprotozoal activity of drugs

| | Concentration, µg/ml | |
|---|---|---|
| The drug | MIC | $IC_{50}$ (95% confidence interval) |
| Compound I | 25 | 59 (56-61) |
| Benzalconium chloride | 30 | 67 (66-69) |
| Miramistin | 50 | 92 (90-94) |
| Chlorhexidine | 20 | 42 (41-43) |

Example 6. In Vitro Study of the Antifungal Activity of Compound I

The study of the antifungal activity of compound I in vitro was carried out in accordance with [Metodicheskiye rekomendatsii No 2. Mikologicheskoye issledovaniye ob"yektov okruzhayushchey sredy i opredeleniye protivogribkovoy aktivnosti razlichnykh veshchestv.—GOU DPO SPbMAPO NII meditsinskoy mikologii im. P. N. Kashkina, GBOU VPO SZGMU im. I. I. Mechnikova Minzdrava. SPb.: Izd. Dom SPbMAPO.—2008.—S. 16. Methodological recommendations No 2. Mycological examination of environmental objects and determination of antifungal activity of various substances.—State Educational Institution of St. Petersburg Medical Academy of Postgraduate Education with Scientific Research Institute of Medical Mycology named after P. N. Kashkin, State Educational Institution of Higher Professional Education North-West State Medical University named after I. I. Mechnikov, Ministry of Health. St. Petersburg.:: Publishing House SPbMAPO.—2008.—P. 16].

The study of the antifungal activity of substances in vitro was carried out in a liquid nutrient medium (Saburo glucose broth) in biological tubes by the method of 2-fold serial dilutions. In test tubes, three parallel series of dilutions of the test substance were prepared in the following way.

Saburo's liquid broth was sterilely poured in 3 ml into each tube; 4.5 ml was poured into the first tube of the row. A total of 14 tubes were used in a row; of which the last was a control one. 400 mg of the test substance was taken as a standard sample and dissolved in 10 ml of distilled water. Thus, the initial dilution contained the test substance at a concentration of 40000 ug/ml. Then 0.5 ml of this dilution was introduced into the first test tube of the series (with 4.5 ml of medium), thereby diluting the concentration of the substance by another 10 times. Therefore, the first tube of the series contained 4000 µg/ml of the test substance. Then, 3 ml of the solution was taken from the first tube and transferred to the second tube, thoroughly purged, then 3 ml of the solution were taken again from the second tube and transferred to the third tube, etc.; from the penultimate tube, 3 ml was poured. The substance was not added to the last tube, as it was the control one. Thus, the following dilutions in µg/ml were obtained: 4000; 2000; 1000; 500; 250; 125; 62.5; 31.2; 15.6; 7.8; 3.9; 1.9. The growth of cultures was initially assessed visually, comparing the growth of microorganisms in the presence of test compounds with the growth of culture without them. The presence of microorganism growth in the liquid medium (opacity or mycelium formation) indicated that the concentration of the test substance was insufficient to suppress its viability. The first lowest concentration of the substance (from a series of consecutive dilutions), where the growth of fungi was suppressed or not visually determined, was considered the minimum inhibitory concentration (MIC).

For the preparation of inoculum, were respectively used pure (2-5) days cultures of yeast and mycelial fungi, grown on Saburo's dense nutrient broth. Inoculum for plating was prepared in different ways, depending on the type of fungi. Thus, yeast cultures of Candida albicans RCPF Y-401/ NCTC-885-653 (C. albicans) were prepared by washing the culture from an agar stroke. Cultures of mycelial fungi Rhizopus oryzae RCPF F-1537/1722 (Rh. Oryzae), Aspergillus fumigates RCPF F-1248/880 (Asp. fumigatus) were pre-degraded in a pounder. A suspension of microorganisms was prepared in a sterile isotonic sodium chloride solution, bringing the inoculum density to 2 billion according to the MacFarland standard ($2 \cdot 10^8$ CFU/ml), given that the size of the fungal elements is about 10 times the size of bacteria. The final cell concentration in the experiment was $(1-5) \times 10^3$ for yeast fungi and $(0.4-5.0) \times 10^4$ for mycelium. The inoculum was used within 15 minutes after preparation; the purity of the fungal strains was monitored before each experiment.

In tubes with three parallel rows of dilutions of the test substance (as described above) and in control tubes in the absence of test substances, one drop of the inoculum suspension was added using a titrated pipette containing 25 drops in 1 ml. After plating, the tripod was shaken vigorously and placed in a thermostat with a temperature of 27° for (2-4) days for yeast fungi and (7-14) days for mycelial fungi, respectively.

The growth of cultures was assessed visually using a step scale, comparing the growth of microorganisms in the presence of test compounds with the growth of culture without them.

0=optical transparency, complete visual absence of growth;
1=weak growth (25% of the control level);
2=significant inhibition of growth (50% of the control level);
3=weak growth inhibition (75% of control level)
4=no growth inhibition For the MIC was taken the minimum concentration of the studied compounds, providing complete inhibition of the visible growth of the studied strains of microorganisms (growth scale=0).

As a result of the study, the MIC values of the test compound I, which has a pronounced fungicidal activity against all types of microscopic fungi, were determined. Miramistin exhibits comparable activity against Asp. fumigates and Rh. nigricans, while being inactive for C. albicans. Benzalkonium chloride in relation to all types of fungi was significantly more active than compound I and miramistin.

The results are presented in tables 4 and 5.

Taking into account the advisability of presenting tabular materials in the text, the applicant has left their description in the text, because this simplifies the understanding of application materials.

TABLE 4

MIC values of test substances for mycelial and yeast species of fungi

| | | The value of the MIC, µg/ml | | |
|---|---|---|---|---|
| No | Strains | I | Benzalconium chloride | Miramistin |
| 1 | C. albicans RCPF Y-401/NCTC-885-653 | 62.5 | 7.8 | >500 |
| 2 | Asp. fumigates RCPF F-l248/880 | 62.5 | 15.6 | 31.2 |
| 3 | Rh. nigricans RCPFF-l537/1722 | 62.5 | 15.6 | 62.5 |

TABLE 5

Determination of MIC of test substances for mycelial and yeast species of fungi

| Strains | Compounds | Concentration, µg/ml | | | | | | | | | | |
|---|---|---|---|---|---|---|---|---|---|---|---|---|
| | | 2000 | 1000 | 500 | 250 | 125 | 62.5 | 31.2 | 15.6 | 7.8 | 3.9 | 1.9 |
| C. albicans | I | − | − | − | − | − | − | +/− | + | + | ++ | ++ |
| Asp. fumigates | | − | − | − | − | − | − | + | + | ++ | +++ | +++ |
| Rh. oryzae | | − | − | − | − | − | − | +/− | + | ++ | +++ | +++ |
| C. albicans | Benzalconium chloride | − | − | − | − | − | − | − | − | − | +/− | + |
| Asp. fumigates | | − | − | − | − | − | − | − | − | +/− | + | + |
| Rh. oryzae | | − | − | − | − | − | − | − | − | + | ++ | ++ |
| C. albicans | Miramistin | − | − | +/− | +/− | + | ++ | +++ | +++ | +++ | +++ | +++ |
| Asp. fumigates | | − | − | − | − | − | − | − | +++ | +++ | +++ | +++ |
| Rh. oryzae | | − | − | − | − | − | − | ++ | +++ | +++ | +++ | +++ |

Example 7. Determination of the Sensitivity of Microscopic Fungi to Compound I in Solution For the preparation of inoculum, were respectively used pure (2-5) days cultures of yeast and mycelial fungi, grown on Saburo's dense nutrient broth. Inoculum for plating was prepared in different ways, depending on the type of fungi. Thus, yeast crops (C. albicans) were prepared by washing the culture from an agar stroke. Cultures of mycelial fungi (Rh. oryzae, Asp. fumigatus) were pre-degraded in a pounder. A suspension of microorganisms was prepared in a sterile isotonic sodium chloride solution, bringing the inoculum density to 5 UNITS (GISK [State Research Institute of Standardization and Control] named after L. A. Tarasevich) or according to the McFarland standard 1 UNIT with a concentration of at least $1 \times 10^6$ CFU/ml, considering that the size of the fungal elements is approximately 10 times the size of bacteria (this provided the possibility of creating a mixture of biocide with suspension, the concentration of microorganisms of the order of $1 \times 10^5$ CFU/ml).

Solutions of compound I, miramistin, and benzalkonium chloride in working concentrations (0.1%, 0.2%, 0.3%) were poured into sterile 0.9 ml tubes. 0.1 ml of microbial suspension was added to test tubes with disinfectant solutions and mixed by shaking for several seconds. The exposition lasted for 1, 5, and 15 minutes. After required temporary exposure for action of the disinfectant, 0.5 ml of the neutralizer solution was added and mixed by shaking.

Then, 0.1 ml of the mixture was inoculated on a dense nutrient medium and the plates with inoculate were placed in a thermostat with a temperature of 27° C. for (2-4) days for yeast and (5-7) days for mycelial fungi, respectively.

In parallel with the experiment, the following controls were set:

1) control of vitality of the microorganism (plating microbial culture on the nutrient medium);

2) control of sterility of the disinfectant solution without adding culture (plating prepared disinfectant solution on a nutrient medium);

3) control of the completeness of neutralization of the disinfectant (1—a neutralizer was added to the solution of the disinfectant (D), 2—a microbial suspension was added to the resulting mixture, 3—the mixture was kept with the necessary exposure, 4—the mixture was plated on a nutrient medium).

After the time required for the cultivation of microorganisms of this species, the results were counted according to the number of colonies grown on the Petri dish. In the absence of growth, the time for culturing microorganisms was increased by a factor of 2. The grown colonies were subjected to microscopy.

The tested substances were studied on clinical and archival strains of yeast and mycelial fungi. As comparison drugs, drugs commonly used in clinical practice were used: miramistin and benzalconium chloride. After the required exposure time for action of the disinfectant, a series of 0.1 ml mixture was aseptically plated on the surface of a dense nutrient medium in Petri dishes. After the time of cultivation of microorganisms, the results were counted according to the number of colonies grown on the Petri dish. The results are presented in table 6.

TABLE 6

Number of colonies grown in a Petri dish when determining the sensitivity of fungi to compound I, miramistin and benzalkonium chloride in solution with varying exposure times

| Fungi | Drugs | Exposure time, min | | | | | | | | |
|---|---|---|---|---|---|---|---|---|---|---|
| | | 1 | | | 5 | | | 15 | | |
| | | 0.1% | 0.2% | 0.3% | 0.1% | 0.2% | 0.3% | 0.1% | 0.2% | 0.3% |
| C. albicans | I | 3 | — | — | 1 | — | — | — | — | — |
| Asp. fumigates | | — | — | — | 1 | — | — | — | — | — |
| Rh. Oryzae | | 1 | — | — | — | — | — | — | — | — |
| C. albicans | Miramistin | 12 | 5 | — | 7 | — | — | — | — | — |
| Asp. fumigates | | 20 | 10 | — | 12 | — | — | 2 | — | — |
| Rh. Oryzae | | 12 | 2 | 1 | 10 | 4 | — | 2 | — | — |
| C. albicans | Benzalconium chloride | — | — | — | — | — | — | — | — | — |
| Asp. fumigates | | — | — | — | — | — | — | — | — | — |
| Rh. Oryzae | | 1 | — | — | — | — | — | — | — | — |

The results of this study showed that compound I is superior to miramistin in its fungicidal effect and is slightly inferior to benzalkonium chloride. Compound I has a pronounced activity for all species at a concentration of 0.2%, while miramistin was not active even at a concentration of 0.3% on Rh. oryzae.

Thus, according to the results obtained, compound I and benzalkonium chloride have the same antifungal activity at a concentration of 0.2% with an exposure of 5 minutes.

Example 8. Determination of Disinfectant Activity of Compound I in Suspension Test To prepare a bacterial suspension of the culture, microorganisms grown in dense nutrient medium for (18-24) hours were washed off with a sterile isotonic sodium chloride solution. The bacterial suspension of each microorganism was brought to a turbidity corresponding to a concentration of $1\times10^9$ cells/ml, which corresponds to 3 units of McFarland. For experiments with protein loading, a solution of bovine serum albumin (BSA) was added to the bacterial suspension to a final concentration of 0.2%.

Solutions of compound I, miramistin, and benzalkonium chloride were poured at a working concentration (0.1%, 0.2%) into a 24-well plate of 0.9 ml per well: 0.1 ml of microbial suspension was added to wells with disinfectant solutions and mixed by shaking for several seconds.

At the end of 1, 5, and 15 minutes of exposure, 0.5 ml of a universal neutralizer was added and mixed by shaking to deactivate the drugs and stop their antimicrobial activity. The neutralizer consisted of tween-80 (Sigma-Aldrich)—3.0 ml, saponin (DIAEM)—3.0 g, histidine—0.1 g, cysteine—0.1 g in 100 ml of phosphate-buffered solution.

The liquid was inoculated on a dense nutrient medium (Müller-Hinton agar) in 0.1 ml of the mixture, cultivation was carried out (24-48) hours at 37° C. Müller-Hinton broth was prepared from dry media (Mueller Hinton broth, Acumedia, Baltimore), cultivation was carried out on agarized Müller-Hinton broth, which included an additional 2% of agar. The media were autoclaved at 121° C. for 15 minutes.

In parallel with the experiment, the following controls were set:

control of vitality of the microorganism (plating microbial culture on the nutrient medium);

control of sterility of the disinfectant solution without adding culture (plating prepared disinfectant solution on a nutrient medium);

control of the completeness of neutralization of the disinfectant (a neutralizer is added to the disinfectant solution, a microbial suspension is added to the resulting mixture, the required exposure time is maintained and the mixture is plated on a nutrient medium).

After the time required for the cultivation of microorganisms, the results were counted according to the number of colonies grown on the Petri dish. In the absence of growth, the time for culturing microorganisms was increased by a factor of 2 (for example, when the cultivation time was 24 hours, it was left in the thermostat for up to 2 days). The experiment was carried out three times under the same conditions.

The criterion of efficacy of drugs in suspension is the death of 100% test microorganisms, with a duration of action not more than 30 minutes.

As a result of the study of the disinfecting ability of a 0.1% solution of compound I in suspension, a death of 99.99% Staphylococcus aureus ATCC 209p was observed. At a concentration of 0.2% in experiments with protein loading and exposure for 15 minutes, compound I caused the death of 100% of bacteria, which meets the criterion of the effectiveness of disinfectants. The disinfecting activity of compound I is slightly lower than the activity of benzalkonium chloride, in which 100% bacterial death at a protein load was detected after 1 minute, and higher than miramistin, for which 100% bacterial death at a protein load was not achieved after 15 minutes exposure (tables 7 and 8).

TABLE 7

The sensitivity of *Staphylococcus aureus* ATCC 209p to 0.1% solutions of compound I, miramistin and benzalkonium chloride in suspension with varying exposure times, n = 3

| | Inhibition rate (M ± SD) *Staphylococcus aureus* ATCC 209p | | | | | |
|---|---|---|---|---|---|---|
| | Exposure time, min | | | | | |
| | 1 | | 5 | | 15 | |
| The drug | −BSA | +BSA | −BSA | +BSA | −BSA | +BSA |
| 0.1% I | 99.99 | 99.99 | 99.99 | 99.99 | 99.99 ± 0.005 | 99.99 ± 0.005 |
| 0.1% Benzalconium chloride | 99.99 | 99.99 | 99.99 | 99.99 | 99.99 ± 0.005 | 99.99 ± 0.005 |
| 0.1% Miramistin | 99.9 | 99.99 | 99.99 | 99.99 | 99.99 | 99.99 ± 0.005 |

−BSA—Protein-free BSA study
+BSA—BSA study with protein load

TABLE 8

The sensitivity of *Staphylococcus aureus* ATCC 209p to 0.2% solutions of compound I, miramistin and benzalkonium chloride in suspension with varying exposure times, n = 3

| | Inhibition rate (M ± SD) *Staphylococcus aureus* ATCC 209p | | | | | |
|---|---|---|---|---|---|---|
| | Exposure time, min | | | | | |
| | 1 | | 5 | | 15 | |
| The drug | −BSA | +BSA | −BSA | +BSA | −BSA | +BSA |
| 0.2% I | 100 | 99.99 ± 0.005 | 100 | 99.99 ± 0.005 | 100 | 100 |
| 0.2% Benzalconium chloride | 100 | 100 | 100 | 100 | 100 | 100 |
| 0.2% Miramistin | 99.9 | 99.99 | 99.99 | 99.99 ± 0.005 | 100 | 99.99 ± 0.005 |

In experiments with protein load, exposure for 15 minutes with compound I and benzalkonium chloride in concentrations of 0.1% resulted in the death of 100% *Escherichia coli* CDC F-50 (table 9). At a concentration of 0.2%, miramistin also managed to show 100% disinfectant activity at a 15-minute exposure (table 10).

TABLE 9

Sensitivity of *Escherichia coli* CDC F-50 to 0.1% solutions of compound I, miramistin and benzalkonium chloride in suspension with varying exposure time, n = 3

| | Inhibition rate (M ± SD) of *Escherichia coli* CDC F-50 growth | | | | | |
|---|---|---|---|---|---|---|
| | Exposure time, min | | | | | |
| | 1 | | 5 | | 15 | |
| The drug | −BSA | +BSA | −BSA | +BSA | −BSA | +BSA |
| 0.1% I | 99.99 | 99.99 ± 0.005 | 99.99 ± 0.005 | 99.99 ± 0.005 | 100 | 100 |
| 0.1% Benzalconium chloride | 99.99 | 99.99 ± 0.005 | 99.99 ± 0.005 | 99.99 ± 0.005 | 100 | 100 |
| 0.1% Miramistin | 99.99 | 99.98 ± 0.005 | 99.99 ± 0.005 | 99.99 | 100 | 99.99 ± 0.005 |

TABLE 10

Sensitivity of *Escherichia coli* CDC F-50 to 0.2% solutions of compound I, miramistin and benzalconium chloride in suspension with varying exposure time, n = 3

| | Inhibition rate (M ± SD) of *Escherichia coli* CDC F-50 growth | | | | | |
|---|---|---|---|---|---|---|
| | Exposure time, min | | | | | |
| | 1 | | 5 | | 15 | |
| The drug | −BSA | +BSA | −BSA | +BSA | −BSA | +BSA |
| 0.2 % I | 99.99 | 99.99 ± 0.005 | 99.99 | 99.99 | 100 | 100 |
| 0.2% Benzalconium chloride | 99.99 ± 0.005 | 99.99 ± 0.005 | 99.99 ± 0.005 | 100 | 100 | 100 |
| 0.2% Miramistin | 99.99 | 99.99 | 99.99 ± 0.005 | 99.99 | 100 | 100 |

Thus, compound I exhibits a disinfecting activity that is comparable to or slightly lower than benzalkonium chloride and higher than that of miramistin.

Example 8. Determination of the Disinfectant Activity of Compound I in a Contaminated Metal Surface Test The preparation of the bacterial suspension was carried out similarly to the procedure for determining the disinfecting activity of compound I in suspension (see example 7). To simulate protein contamination of the metal surface, a BSA solution was added to the bacterial suspension to a final concentration of 0.4%. The surface of the metal table was drawn into squares, the number of which depended on the number of strains studied. The test surface should be clean, intact, sterile. To do this, the table was cleaned with alcohol, and then with sterile water. A microbial suspension in a volume of 0.125 ml was applied to a surface area of 5×5 cm and distributed with a sterile spatula over the entire square area. After the microbial suspension was dried, a 0.5 ml solution of compound I (miramistin and benzalkonium chloride being a control) was uniformly applied to the surface at a working concentration of 0.1 and 0.2% and distributed over the square surface with a sterile spatula, and then kept for 1, 5, and 15 minutes.

After the end of exposure, the contaminated surface was thoroughly wiped with a sterile gauze cloth (size 5×5 cm) soaked in 1 ml of a neutralizer solution and the cloth was immersed in 10 ml of sterile physiological saline in a flask, which was shaken for 10 minutes.

Plating was carried out as in example 7, in addition to the controls were carried out:
control of the sterility of the surface (before applying the microbial suspension, a metal table was washed off with a sterile swab, followed by plating on a nutrient medium);
control of the vitality of the microorganism (after applying microbial suspension on the metal table, it was washed off with a sterile swab with subsequent plating on the nutrient medium).

The contamination density of 1 $cm^2$ of the surface and the percentage of disinfection were calculated, taking the number of colonies removed from control surfaces as 100%. The criterion for the effectiveness of surface disinfection is not less than 99.99% of the death of test microorganisms, the disinfection time is not more than 120 minutes.

When 0.1% solutions of compound I, miramistin and benzalkonium chloride were kept on a metal surface contaminated with *Staphylococcus aureus* ATCC 209p, effective inhibition of bacterial growth (99.99%) was observed in all three preparations 5 minutes after application (table 11). When exposed to compound I at a concentration of 0.2%, effective inhibition of bacterial growth (comparable to benzalkonium chloride and more effective than miramistin) occurred after 1 minute (table 12).

TABLE 11

The sensitivity of *Staphylococcus aureus* ATCC 209p to 0.1% solutions of compound I, miramistin and benzalconium chloride on metal surface with varying exposure times, n = 3

| | Inhibition rate (Mean ± SD) of *Staphylococcus aureus* ATCC 209p growth | | | | | |
|---|---|---|---|---|---|---|
| | Exposure time, min | | | | | |
| | 1 | | 5 | | 15 | |
| The drug | −BSA | +BSA | −BSA | +BSA | −BSA | +BSA |
| 0.1% I | 99.99 | 99.98 ± 0.00 | 99.99 | 99.99 | 99.99 | 99.99 |
| 0.1% Benzalconium chloride | 99.99 | 99.99 ± 0.005 | 99.99 | 99.99 | 99.99 ± 0.005 | 99.99 |
| 0.1% Miramistin | 99.98 ± 0.005 | 99.98 ± 0.00 | 99.99 | 99.99 | 99.99 | 99.99 |

TABLE 12

The sensitivity of *Staphylococcus aureus* ATCC 209p to 0.2% solutions of compound I, miramistin and benzalkonium chloride on metal surface with varying exposure times, n = 3

| | Inhibition rate (M ± SD) *Staphylococcus aureus* ATCC 209p | | | | | |
|---|---|---|---|---|---|---|
| | Exposure time, min | | | | | |
| | 1 | | 5 | | 15 | |
| The drug | −BSA | +BSA | −BSA | +BSA | −BSA | +BSA |
| 0.2 % I | 99.99 | 99.99 | 99.99 | 99.99 | 99.99 | 99.99 |
| 0.2% Benzalconium chloride | 99.99 | 99.99 | 99.99 | 99.99 | 100 | 99.99 ± 0.005 |
| 0.2% Miramistin | 99.98 ± 0.005 | 99.98 ± 0.00 | 99.99 | 99.99 | 99.99 | 99.99 |

When 0.1% solutions of compound I, miramistin and benzalkonium chloride were exposed for 1, 5, and 15 minutes on a metal surface contaminated with *Escherichia coli* CDC F-50, effective inhibition of bacterial growth was observed only 15 minutes after application of the preparations (table 13). At a concentration of 0.2%, effective inhibition of bacterial growth in three drugs occurs after 5 minutes, and in the test without protein load in benzalkonium chloride after 1 minute (table 14).

TABLE 13

Sensitivity of *Escherichia coli* CDC F-50 to 0.2% solutions of compound I, miramistin and benzalconium chloride on metal surface with variation of exposure time, n = 0.1

| | Inhibition rate (M ± SD) of *Escherichia coli* CDC F-50 growth | | | | | |
|---|---|---|---|---|---|---|
| | Exposure time, min | | | | | |
| | 1 | | 5 | | 15 | |
| The drug | −BSA | +BSA | −BSA | +BSA | −BSA | +BSA |
| 0.1% I | 99.92 ± 0.005 | 99.92 ± 0.005 | 99.97 ± 0.005 | 99.96 ± 0.005 | 99.99 ± 0.00 | 99.99 ± 0.005 |
| 0.1% Benzalconium chloride | 99.96 ± 0.005 | 99.97 ± 0.005 | 99.98 ± 0.005 | 99.97 ± 0.005 | 100 ± 0.00 | 99.99 ± 0.005 |
| 0.1% Miramistin | 99.75 ± 0.00 | 99.75 ± 0.005 | 99.86 ± 0.005 | 99.97 ± 0.005 | 99.99 ± 0.005 | 99.99 ± 0.005 |

TABLE 14

Sensitivity of *Escherichia coli* CDC F-50 to 0.2% solutions of compound I, miramistin and benzalconium chloride on metal surface with variation of exposure time, n = 3

| | Inhibition rate (M ± SD) of *Escherichia coli* CDC F-50 growth | | | | | |
|---|---|---|---|---|---|---|
| | Exposure time, min | | | | | |
| | 1 | | 5 | | 15 | |
| The drug | −BSA | +BSA | −BSA | +BSA | −BSA | +BSA |
| 0.2 % I | 99.98 ± 0.005 | 99.94 ± 0.00 | 99.99 ± 0.005 | 99.99 ± 0.005 | 100 | 100 ± 0.005 |
| 0.2% Benzalconium chloride | 99.99 ± 0.005 | 99.97 ± 0.00 | 100 | 99.99 ± 0.005 | 100 | 100 ± 0.00 |
| 0.2% Miramistin | 99.98 ± 0.005 | 99.83 ± 0.005 | 99.99 ± 0.005 | 99.99 ± 0.005 | 100 | 99.99 ± 0.005 |

Thus, the disinfectant activity of compound I is comparable, or slightly lower than that of benzalkonium chloride and higher than that of miramistin.

Example 9. The Study of the Antiseptic Activity of Compound I

The study of the antiseptic activity of compound I in rats with intragastric administration was carried out in accordance with [R 4.2.2643-10 *Metody laboratornykh issledovaniy i ispytaniy mediko-profilakticheskikh dezinfektsionnykh sredstv dlya otsenki ikh effektivnosti i bezopasnosti: Rukovodstvo.—M: Federal'nyy tsentr gigiyeny i epidemiologii Rospotrebnadzora*, 2010.—S. 615. R 4.2.2643-10 Laboratory methods for the study and testing of medical prophylactic disinfectants to assess their effectiveness and safety: Guide.—M.:: Federal Center for Hygiene and Epidemiology of Rospotrebnadzor, 2010.—P. 615]. Experiments were carried out on male Wistar rats with a body weight of 180-250 g.

A culture of *E. coli* CDC F-50, grown on dense nutrient medium for (18-20) hours, was washed with sterile isotonic chloride solution, centrifuged at 5000 rpm for 5 minutes, the supernatant was drained and cells were resuspended with sterile isotonic sodium chloride solution.

The bacterial suspension of microorganisms was brought to a turbidity of 0.05 according to McFarland, which corresponds to a concentration of $1.5 \times 10^7$ cells/ml.

Animals were formed in 5 groups of 6 animals each. All manipulations with animals were performed under isoflurane anesthesia (4%—induction of anesthesia (2 min, 1 l/min), 2%—basis narcosis). A portion of 5×5 cm was shaved with a hair clipper on the dorsal part of the body of the animal.

A 0.25 ml microbial suspension containing $1 \times 10^7$ CFU of *E. coli* CDC F-50 was applied to the shaved portion of the rat back with a dispenser and distributed with a sterile disposable spatula over the entire square area. It was left for 2-3 minutes until dry.

Then, a gauze cloth (5×5 cm) was applied to the skin of rats for 5 minutes. In the experimental group, the tissue was pre-wetted with 1 ml of 0.2% solution of compound I, and in the positive control groups, the tissue was dipped in 1 ml of 0.2% miramistin, benzalkonium chloride and chlorhexidine. In the negative control group, the cloth was immersed in 1 ml of sterile saline.

At the end of the exposure time with an antiseptic, to stop its effect on the microorganism, a universal neutralizer was used, consisting of tween-80—3.0 ml, saponin—3.0 g, histidine—0.1 g, cysteine—0.1 g, brought up to 100 ml with phosphate-buffered solution The rat skin was washed off (within 1-3 seconds) with a sterile gauze cloth (5×5 cm) moistened with a sterile neutralizer solution. Then the cloth was immersed in 10 ml of sterile saline in a falcon, which was shaken for 10 minutes.

After that, the washing liquid was plated in 2-3 dishes of 0.1 ml each in a dense nutrient medium (Müller-Hinton agar), cultivation was carried out for 24-48 hours at 37° C. Müller-Hinton broth was prepared from dry media (Mueller Hinton broth, Acumedia, Baltimore), cultivation was carried out on agarized Müller-Hinton broth, which included an additional 2% of agar. The media were autoclaved at 121° C. for 15 minutes.

After the time required for the cultivation of microorganisms of this species, the results were counted according to the number of colonies grown on the Petri dish. The results were taken into account by assessing the residual contamination of surfaces after treatment with an antiseptic solution. After counting the number of colonies grown on Petri dishes, the density of contamination per 1 cm² of the surface and the percentage of disinfection were calculated, taking the number of colonies removed from control surfaces and not exposed to antiseptics action as 100%. The percentage of growth inhibition of *E. coli* CDC F-50 was calculated by the formula:

$$I = 100\% \frac{O \times 100\%}{K}, \text{ where}$$

$I$—percentage of growth inhibition %

$K$—the number of colonies in the control group of animals $O$—the number of colonies in the experimental group.

An in vivo study of antiseptic properties revealed that compound I reduces CFU of *E. coli* CD CF-50 on rat skin after 5 minutes of exposure. No statistically significant differences were found with benzalkonium chloride, miramistin, and chlorhexidine (Table 15).

TABLE 15

Inhibition of growth of *E. coli* CDC F-50 (CFU/cm²) at an antiseptic concentration of 0.2% and an exposure time of 5 min on rat skin, n = 6

| The drug | Growth inhibition rate (M ± SD) |
|---|---|
| I, 0.2% | 97.5 ± 1.7 |
| Benzalconium chloride, 0.2% | 96.8 ± 2.0 |
| Miramistin, 0.2% | 97.2 ± 1.8 |
| Chlorhexidine, 0.2% | 95.7 ± 3.4 |

Example 10. Determination of Acute Toxicity of Compound I in Mice after Intragastric Administration The study was performed on mice of the CD-1 (ICR) line (6-8 weeks, weight not less than 18 g) of both sexes. Intragastric (oral) administration of a solution of compound I in a volume of not more than 0.5 ml/30 g body weight of the mouse using a gastric tube was used. Mice administered doses were 3000 mg/kg, 2000 mg/kg, 1000 mg/kg, 500 mg/kg and 50 mg/kg.

According to the results of the acute toxicity study of compound I when administered orally (table 16) in accordance with GOST 32644-2014, the studied drug can be attributed to the 4th toxicity class according to the Globally Harmonized System of Classification of Hazards and Labeling of Chemical Products, and in accordance with GOST 12.1.007-76—to the 3rd class of moderately hazardous harmful substances.

TABLE 16

Results of compound I acute toxicity study on mice

| Animal species | Dose, mg/kg | Number of died animals in the group | $LD_{16}$ | $LD_{50}$ (95% confidence interval) | $LD_{86}$ |
|---|---|---|---|---|---|
| Mice CD-1 | 3000 2000 | 4/4 5/10 | 788 | 1706 (1194-2470) | 2623 |

TABLE 16-continued

Results of compound Iacute toxicity study on mice

| Animal species | Dose, mg/kg | Number of died animals in the group | $LD_{16}$ | $LD_{50}$ (95% confidence interval) | $LD_{86}$ |
|---|---|---|---|---|---|
| | 1000 | 3/6 | | | |
| | 500 | 0/6 | | | |
| | 50 | 0/6 | | | |

Thus, from the above it can be concluded that the claimed compound exhibits a high level of antibacterial, antimycotic, antiviral and antiprotozoal activity. An important advantage of compound I is high safety. Studies of acute toxicity in mice with intragastric administration have shown $LD_{50}$ for compound I to be 1,706 mg/kg. Currently widely used antiseptics miramistin ($LD_{50}$=1000 mg/kg) [Pat. 2161961 Russian Federation, MPK[7], Cl, A 61 K 31/14, A 61 P 31/00. Medicinal preparation/Krivoshein Y. S., Rudko A. P.; applicant and patent holder Krivoshein Y. S., Rudko A. P.—No 2000106427/14; application 17.03.2000M published 20 Jan. 2001], benzalkonium chloride ($LD_{50}$=150 mg/(kg) [Benzalkonium chloride. Kemsol MOSS-KILL safety data sheet] and chlorhexidine ($LD_5O$=1260 mg/kg) [0.05% % Chlorhexidine & 0.5% Cetrimide Aqueous Irrigation Pfizer material safety data sheet.] in intragastric administration on mice are significantly more toxic. In general, the claimed technical solution allows to create a new highly effective and safe antiseptic drug, which potentially will significantly improve the quality and life expectancy of patients.

The claimed technical solution meets the criterion of "novelty" applied to the inventions, as the studied level of technology did not identify technical solutions that have the stated set of distinctive features that ensure the achievement of the stated results.

The claimed technical solution meets the criterion of "inventive step" applied to the inventions, as it is not obvious to a person skilled in this field of science and technology.

The claimed technical solution meets the criterion of "industrial applicability", as it can be implemented at any specialized enterprise using standard equipment, well-known domestic materials and technologies.

What is claimed is:

1. Quaternary ammonium salt of formula I:

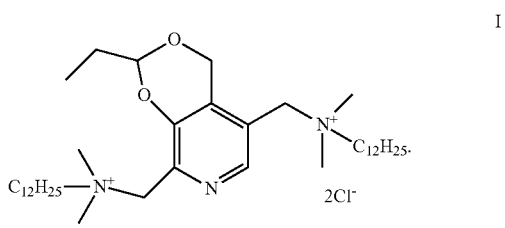

2. The quaternary ammonium salt according to claim 1 the salt having antibacterial activity.

3. The quaternary ammonium salt according to claim 1, the salt having antimycotic activity.

4. The quaternary ammonium salt according to claim 1, the salt having antiviral activity.

5. The quaternary ammonium salt according to claim 1, the salt having antiprotozoic activity.

* * * * *